US00PP20184P2

(12) United States Plant Patent
Unger

(10) Patent No.: US PP20,184 P2
(45) Date of Patent: Jul. 28, 2009

(54) ***SALVIA* PLANT NAMED 'SAL CARD 07'**

(50) Latin Name: *Salvia nemorosa*
Varietal Denomination: SAL CARD 07

(76) Inventor: Christiaan Unger, Robert Koch Strasse 7, 67511 Worms (DE)

( * ) Notice: Subject to any disclaimer, the term of this patent is extended or adjusted under 35 U.S.C. 154(b) by 85 days.

(21) Appl. No.: 11/824,142

(22) Filed: Jun. 30, 2007

(51) Int. Cl.
*A01H 5/00* (2006.01)

(52) U.S. Cl. ..... Plt./475

(58) Field of Classification Search ..... Plt./475
See application file for complete search history.

(56) References Cited

U.S. PATENT DOCUMENTS

PP13,322 P2 * 12/2002 Haussermann ..... Plt./475

* cited by examiner

*Primary Examiner*—Wendy C. Haas

(57) ABSTRACT

A new and distinct *Salvia* plant cultivar is disclosed, characterized by an upright, vigorous growth habit; violet-blue flowers; dark green foliage; and a year round flowering habit.

2 Drawing Sheets

Latin name of the genus and species: *Salvia nemorosa.*
Variety denomination: 'SAL CARD 07'.

BACKGROUND OF THE INVENTION

The new cultivar is a product of open pollination in a heterogeneous population in 2003. The resulting seeds were grown and 'SAL CARD 07' was discovered as a single plant by Christiaan Unger in July 2004 in a cultivated area of Rheinfelden, Germany.

Asexual reproduction of the new cultivar 'SAL CARD 07' by vegetative cuttings was performed in Oxnard, Calif., and has shown that the unique features of this cultivar are stable and reproduced true to type on successive generations.

SUMMARY OF THE INVENTION

The cultivar 'SAL CARD 07' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAL CARD 07.' These characteristics in combination distinguish 'SAL CARD 07' as a new and distinct *Salvia* cultivar:

1. Upright, vigorous growth habit;
2. Violet-blue flowers;
3. Dark green foliage; and
4. A year round flowering habit.

Plants of the new cultivar differ from plants of the parent selections primarily in inflorescence size and level of heat tolerance.

In comparison to the commercially available variety 'Haeumanarc' (U.S. Plant Pat. No. 13,322), 'SAL CARD 07' is taller and has a wider plant spread. Additionally, 'SAL CARD 07' has darker green foliage. Finally, the inflorescences of 'SAL CARD 07' are a lighter violet-blue than the inflorescences of the comparable variety.

BRIEF DESCRIPTION OF THE PHOTOGRAPH

The photograph on the first sheet illustrates a close-up view of the flowers of 'SAL CARD 07'.

The photograph on the second sheet illustrates an overall view in full color a typical plant of 'SAL CARD 07' grown in an outdoor garden.

The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'SAL CARD 07' plants grown in Oxnard, Calif. during the months of January through June in an outdoor garden. The growing temperature ranged from 12° C. to 15° C. at night to 12° C. to 20° C. during the day. Measurements and numerical values represent averages of typical flowering types.

Botanical classification: *Salvia nemorosa* cultivar 'SAL CARD 07.'
Commercial classification: Sage.

PROPAGATION

Time to rooting: 10 to 13 days at 20° C.
Root description: Fine, fibrous.

PLANT

Growth habit: Upright herbaceous perennial.
Height: Approximately 60 cm.
Plant spread: Approximately 70 cm.
Growth rate: Moderate.
Branching characteristics: Freely branching.
Number of lateral branches: About 12 flowering lateral branches.
Length of lateral branches: Approximately 55 cm.
Number of leaves per lateral branch: Approximately 22.

Internode length: Between 8 and 14 cm.
Age of plant described: Approximately 139 days.

FOLIAGE

Leaf:
*Arrangement.*—Opposite.
*Average length.*—Approximately 4.9 cm.
*Average width.*—Approximately 2.7 cm.
*Shape of blade.*—Ovate.
*Apex.*—Acuminate.
*Base.*—Oblique.
*Attachment.*—Petiolate.
*Margin.*—Crenate.
*Texture of top surface.*—Pubescent.
*Texture of bottom surface.*—Pubescent.
*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
*Venation.*—Type: Pinnate. Venation color upper side: Near Yellow-Green 147B. Venation color under side: Near Yellow-Green 147D.
Petiole:
*Average length.*—Approximately 1.8 cm.
*Color.*—Near Yellow-Green 147B.
*Diameter.*—Approximately 0.1 cm.

FLOWER DESCRIPTION

Flowering season: Year round in Southern California and spring to summer in cooler regions of California.
Inflorescence form: Racemiform.
Flower arrangement: Whorls.
Quantity of flowers: Between 8 and 15 flowers per whorl and between 9 and 14 whorls per raceme.
Distance between whorls: Approximately 1 to 3 cm.
Flower bud:
*Shape.*—Pandurate.
*Color.*—Near Violet-Blue 93C.
*Surface.*—Pubescent.
*Length.*—Approximately 6 mm.
*Diameter.*—Approximately 4 mm.
Corolla tube:
*Shape.*—Tubular.
*Surface.*—Pubescent.
*Color.*—Near Violet-Blue 93C.
Flower dimensions (calyx, corolla tube, and lobes):
*Length.*—Approximately 2.5 cm.
*Diameter.*—Approximately 0.2 cm.
Corolla lobes:
*Quantity.*—Two primary lobes and two reduced lateral lobes.
*Shape.*—Upper lobe falcate and lower lobe spreading.
*Color.*—Near Violet-Blue 93C.
Petals:
*Quantity.*—Two.
*Color.*—Between Violet-Blue 93C.
*Shape.*—Petals are basally fused and spatulate.
Aspect: Facing outward.

Peduncle:
*Length.*—Approximately 20 cm.
*Width.*—Approximately 0.3 cm.
*Surface.*—Pubescent.
*Color.*—Darker than Greyed-Green 189A.
Calyx:
*Shape.*—Tubular-shaped.
*Length.*—Approximately 0.1 cm.
*Diameter.*—Approximately 6 mm.
*Color.*—Outer surface: Near Violet-Blue 93C. Inner surface: Near Violet-Blue 93C.
*Texture.*—Pubescent.
Sepals:
*Quantity.*—Two.
*Fused or unfused.*—Basally fused.
*Color.*—Near Violet-Blue 93B.

REPRODUCTIVE ORGANS

Pistil:
*Quantity.*—One.
*Shape.*—Filiform.
*Length.*—Approximately 12 mm.
*Width.*—Approximately 0.3 mm.
*Color.*—Near Yellow-White 158C.
*Surface.*—Pubescent.
Stigma:
*Shape.*—Two-lobed.
*Length.*—Approximately 4 mm.
*Width.*—Approximately 0.4 mm.
*Color.*—Near Violet-Blue 93B.
Style:
*Shape.*—Filiform.
*Length.*—Approximately 6 mm.
*Width.*—Approximately 3 mm.
*Color.*—Near Yellow-White 158C.
Stamens:
*Quantity.*—Two.
*Length.*—Approximately 2 mm.
*Width.*—Approximately 1 mm.
*Color.*—Near Yellow-White 158C.
Anther:
*Length.*—Approximately 2 mm.
*Width.*—Approximately 1.1 mm.
*Color.*—Near Yellow-White 158C. No pollen has been observed on this variety.
Ovary:
*Length.*—Approximately 1.8 mm.
*Width.*—Approximately 1.1 mm.
*Color.*—Near Yellow-White 158C.

OTHER CHARACTERISTICS

Disease resistance: Neither resistance nor susceptibility to diseases or pests has been observed in this variety.
Drought tolerance/cold tolerance: Tolerate to heat at least up to 30° C. and cool at least down to USDA Zone 5.
Fruit/seed production: Not observed because commercially the plants are discarded or the flowers removed before seed set occurs.

What is claimed is:

1. A new and distinct cultivar of *Salvia* plant named 'SAL CARD 07' as herein illustrated and described.

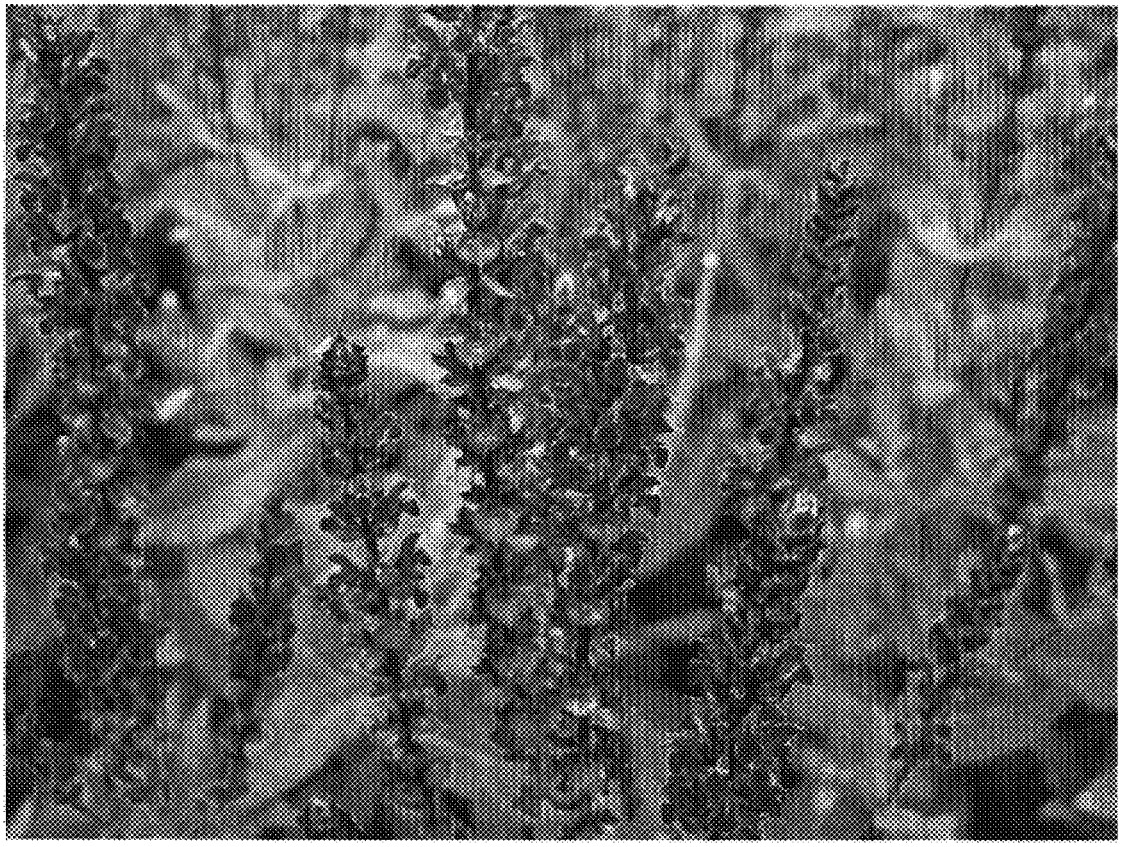

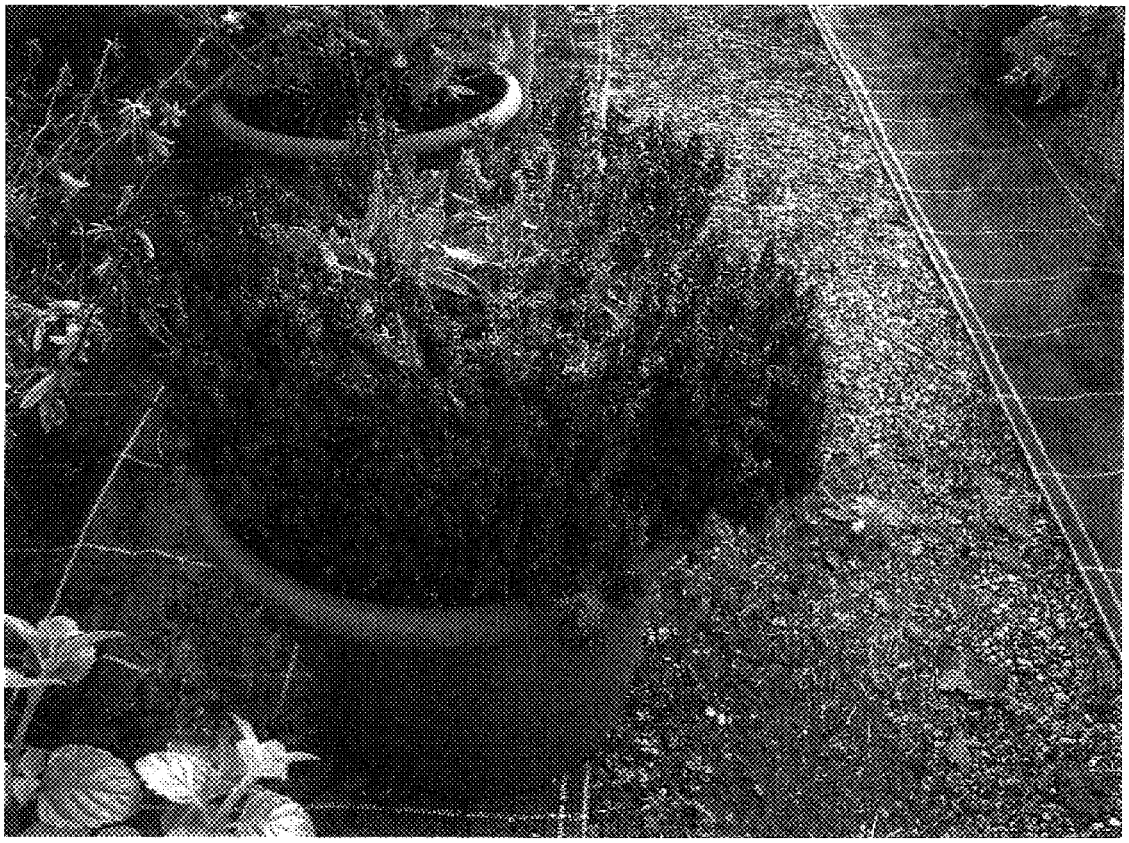

* * * * *